United States Patent

Miller

(10) Patent No.: US 10,039,892 B2
(45) Date of Patent: Aug. 7, 2018

(54) PEDIATRIC INDUCTION OF ANESTHESIA

(71) Applicant: Diane Miller, Fairfax, VA (US)

(72) Inventor: Diane Miller, Fairfax, VA (US)

(*) Notice: Subject to any disclaimer, the term of this patent is extended or adjusted under 35 U.S.C. 154(b) by 689 days.

(21) Appl. No.: 14/667,777

(22) Filed: Mar. 25, 2015

(65) Prior Publication Data

US 2016/0279373 A1  Sep. 29, 2016

(51) Int. Cl.
| | |
|---|---|
| *A61M 16/10* | (2006.01) |
| *A61M 16/00* | (2006.01) |
| *A61M 16/04* | (2006.01) |
| *A61M 16/08* | (2006.01) |
| *A61M 16/01* | (2006.01) |

(52) U.S. Cl.
CPC .......... *A61M 16/049* (2014.02); *A61M 16/01* (2013.01); *A61M 16/0084* (2014.02); *A61M 16/085* (2014.02); *A61M 16/0833* (2014.02); *A61M 2205/183* (2013.01); *A61M 2205/43* (2013.01); *A61M 2205/502* (2013.01); *A61M 2205/59* (2013.01)

(58) Field of Classification Search
CPC .............. A61M 16/0084; A61M 16/01; A61M 16/049; A61M 16/0833; A61M 16/085; A61M 2205/43; A61M 2205/59; A61M 2205/183; A61M 2205/581; A61M 2205/583; A61M 16/00; A61M 16/0057; A61M 16/04; A61M 16/0488; A61M 16/06; A61M 16/0605; A61M 16/0816; A61M 16/0875; A61M 16/10; A61M 16/104; A61M 16/12; A61B 5/087; A61B 5/0873; A61B 5/09; A63H 33/40
See application file for complete search history.

(56) References Cited

U.S. PATENT DOCUMENTS

| | | | | |
|---|---|---|---|---|
| 340,778 | A | * 4/1886 | Gilbert | A61M 16/0084 128/205.13 |
| 1,357,601 | A | * 11/1920 | Walter | A61M 16/18 128/200.13 |
| 1,955,815 | A | 4/1934 | Lauterbach | |
| 2,016,212 | A | * 10/1935 | O'Connell | A61M 16/06 128/207.12 |

(Continued)

FOREIGN PATENT DOCUMENTS

| | | |
|---|---|---|
| EP | WO 2014129993 | 8/2014 |
| WO | WO 2006106328 A1 * 10/2006 | ...... A61M 16/0078 |

OTHER PUBLICATIONS

Meretoja, et al; Sevoflurane-nitrous oxide or halothane-nitrous oxide for paediatric bronchoscopy and gastroscopy; British Journal of Anaesthesia 1996; vol. 76, pp. 767-771; Oxforrn University Press.

(Continued)

*Primary Examiner* — Jackie Tan-Uyen T Ho
*Assistant Examiner* — Joseph D Boecker
(74) *Attorney, Agent, or Firm* — Johnson Legal PLLC

(57) ABSTRACT

Disclosed is a mask-free system and method for inducing anesthesia in a pediatric patient. In a preferred embodiment, calming and then anesthetic gases are administered through a mouthpiece with a distraction device, such as an inflatable bag or balloon or an audible siren whistle. This system avoids the anxieties and trauma of the pediatric patient and their parents that have been associated with mask-based induction methods.

15 Claims, 4 Drawing Sheets

(56) References Cited

U.S. PATENT DOCUMENTS

| | | | |
|---|---|---|---|
| 2,092,942 A | 9/1937 | Trollen | |
| 3,814,091 A | 6/1974 | Henkin | |
| 3,859,997 A | 1/1975 | Douma et al. | |
| 4,360,018 A | 11/1982 | Choksi | |
| 4,809,692 A * | 3/1989 | Nowacki | A61M 15/0086 128/203.29 |
| 4,896,666 A | 1/1990 | Hinkle | |
| 5,591,130 A * | 1/1997 | Denton | A61M 16/0078 128/202.22 |
| 5,598,839 A | 2/1997 | Niles et al. | |
| 5,690,096 A | 11/1997 | Burch | |
| 5,697,363 A | 12/1997 | Hart | |
| 5,743,257 A | 4/1998 | Koehler et al. | |
| 5,803,063 A * | 9/1998 | Corey | A61M 15/00 128/200.14 |
| 5,865,172 A | 2/1999 | Butler et al. | |
| 5,937,852 A | 8/1999 | Butler et al. | |
| 6,073,628 A | 6/2000 | Butler et al. | |
| 6,149,603 A * | 11/2000 | Parker | A61M 16/0488 128/200.24 |
| 6,463,928 B1 * | 10/2002 | Buisson | A61M 16/08 128/203.12 |
| 6,578,571 B1 * | 6/2003 | Watt | A61M 15/00 128/200.14 |
| 6,776,157 B2 | 8/2004 | Williams et al. | |
| 7,353,825 B2 | 4/2008 | Orr et al. | |
| 7,992,555 B2 | 8/2011 | Heinonen et al. | |
| 8,671,934 B2 | 3/2014 | Addington et al. | |
| 2002/0117173 A1 * | 8/2002 | Lynn | A61M 16/0078 128/202.28 |
| 2004/0007231 A1 * | 1/2004 | Zhou | A61M 16/06 128/202.16 |
| 2008/0251082 A1 * | 10/2008 | Sinha | A61M 16/0045 128/207.16 |
| 2009/0044801 A1 * | 2/2009 | Barbosa | A61M 16/0078 128/203.13 |
| 2009/0044802 A1 * | 2/2009 | Barbosa | A61M 16/0078 128/203.13 |
| 2011/0186054 A1 | 8/2011 | Boyd | |
| 2014/0106324 A1 * | 4/2014 | Adams | A61M 15/009 434/262 |

OTHER PUBLICATIONS

Bufalini; Role of interactive music in ontological pediatric patients undergoing painful procedures; Minerva Pediatrica; Aug. 2009; 61 (4): 379-89.

Shawky; A New Friendly Approach to Pediatric Inhaled Induction; Anesthesia & Analgesia; Mar. 2005—vol. 100—Issue 3—pp. 901-902; Published by Lippincott Williams & Wilkins.

Trapp; Techniques for Induction of General Anesthesia in the Pediatric Dental Patient; Anasthesia Progress 1992; 39 (4-5): 138-141; Published by American Dental Society of Anesthesiology.

Kerimoglu, et al; Anesthesia induction using video glasses as a distraction tool for the management of preoperative anxiety in children; Anesthesia & Analgesia; Dec. 2013; 117 (6): 1373-9; Published by Lippincott Williams & Wilkins.

Jolley; Cartoons reduce anxiety during anesthesia induction in children; gasexchange.com; http://gasexchange.com/articles/cartoons-anxiety-anesthesia-induction/.

Vagnoli, et al; Clown doctors as a treatment for preoperative anxiety in children: a randomized, prospective study; Pediatrics Oct. 2005; 116 (4): e563-7; published by American Academy of Pediatrics.

Tan, et al; Anaesthesia for the uncooperative child; Continuing Education in Anaesthesia, Critical Care & Pain—2010; vol. 10 (2): 48-52; Published by Oxford Journals.

Patel, et al; Distraction with a hand-held video game reduces pediatric preoperative anxiety; Paediatric Anaesthesia Oct. 2006; 16 (10): 1019-27.

Aydin, et al; Do not mask the mask: use it as a premedicant; Paediatric Anaesthesia Feb. 2008; 18(2): 107-12.

Lee, et al; Effect of behavioral intervention using smartphone application for preoperative anxiety in pediatric patients; Korean Journal of Anesthesiology Dec. 2013; 65 (6): 508-18.

Duarte, et al; Nitrous Oxide Use in Children; Revista Brasileira De Anestesiologia 2012; 62: 3: 451-467.

Litman; Allaying Anxiety in Children: When a Funny Thing Happens on the Way to the Operating Room; Anesthesiology 2011; 115: 4-5; Published by Lippincott Williams & Wilkins.

Gomez, et al; Efficacy of anesthetic premedication in pediatric patients using oral midazolam and acetaminophen. Observational study; Colombian Journal of Anesthesiology 2013; 41(1):4-9.

Van Den Berg, et al; Inhalational or Intravenous Induction of Anesthesia in Children? An Audit of Patient and Parent Preference; Journal of Anesthesia & Clinical Research; 2011, 2:8.

Huda, et al; Use of Sevoflurane With or Without Nitrous Oxide for Inhalational Induction in Paediatric Patients; Internet Scientific Publications; https://ispub.com/IJA/32/1/1471.

Kain, et al; Parental Presence during Induction of Anesthesia; Anesthesiology 2003; 98: 58-64; American Society of Anesthesiologists.

Kain, et al; Distress During the Induction of Anesthesia and Postoperative Behavioral Outcomes; Anesthesia & Analgesia May 1999; 88(5): 1042-7.

Yip, et al; Non-pharmacological Interventions for Assisting the Induction of Anaesthesia in Children (Review); The Cochrane Library 2010 Issue 11.

Agostini, et al; Parental Anxiety and Stress before Pediatric Anesthesia: A Pilot Study on the Effectiveness of Preoperative Clown Intervention; Journal of Health Psychology May 2014; 19 (5): 587-601.

Department of Pediatric Anesthisiology—Children's Hospital of Pittsburgh of UPMC; www.chp.edu/CHP/PP+Parental+Presence+at+Induction+of+Anesthesia.

Gordon; Pediatric Anesthesia—Induction Principles and Technics—1; www.anesthesiawiki.net/metrohealthanesthesia/MHAnes/edu/ped/inductionl.htm; Aug. 30, 2010.

Bailey Jr, et al; Preinduction Techniques for Pediatric Anesthesia; Current Opinion in Anesthesiology 2005 18: 265-269; Published by Lippincott Williams & Wilkins.

Calipel, et al; Premedication in children: hypnosis versus midazolam; Paediatr Anaesth. Apr. 2005; 15(4): 275-81.

Johns; Preparing Children for Surgery Through Interactive Education; Capstone Paper submitted in partial fulfillment of the requirements for the degree of Doctorate of Nursing Practice, Chatham University; Dec. 14, 2009.

Theanesthesiaconsultant Blog; Smart Phones and Pediatric Anesthesia Induction; http://theanestbesiaconsultant.com/2011/01/18/smart-phones-and-pediatric-anesthesia-induction/; Posted on Jan. 18, 2011.

Mifflin, et al; Streamed video clips to reduce anxiety in children during inhaled induction of anesthesia; Anesthesia & Analgesia Nov. 2012; 115(5): 1162-7.

Seiden, et al; Tablet-based Interactive Distraction (TBID) vs oral midazolam to minimize perioperative anxiety in pediatric patients: a nonineriority randomized trial; Paediatric Anaesthesia Dec. 2014; 24(12): 1217-23.

Vessey, et al; Parental upset associated with participation in induction of anaesthesia in children; Canadian Journal of Anaesthesia Apr. 1994, vol. 41, Issue 4, pp. 276-280.

Zuwala, et al; Reducing Anxiety in Parents Before and During Pediatric Anesthesia Induction; AANA Journal/Feb. 2001/vol. 69, No. 1; pp. 21-25.

* cited by examiner

PEDIATRIC INDUCTION OF ANESTHESIA

FIELD OF THE INVENTION

The invention relates to a mask-free system and method for its use to distract pediatric patients during induction of anesthesia so as to reduce or minimize fear and trauma during the process that is experienced by the patient, parents, caregivers and medical staff.

BACKGROUND OF THE INVENTION

Inhalation mask induction is the standard method for inducing anesthesia in pediatric patients. In the preoperative area many anesthesia care provider make promises to the child of "blowing up balloons" in the operating room. However, during routine mask induction, the anesthesia care provider will place the child on an operating room table in the supine position (on their back), then place a mask over the child's face. The mask is connected to a length of double corrugated tubing (a circuit) that extends back to the anesthesia machine. When the child inhales, a volatile anesthetic is inspired and puts the child to sleep. At the juncture between the corrugated tubing and the anesthesia machine, there is a reservoir bag that collects the expired gases and visibly inflates as the patient exhales. Unfortunately, pediatric patients of an age to be aware of the device often cannot see the reservoir bag due to their position on the table and the fact that they are unable to focus on anything other than the unpleasant smell of the anesthesia gas and the strangers forcibly holding them in place on the OR table.

Anesthesiologists typically use a mask for induction. One reason is that children are traumatized by needles and injections. Another reason is for a desire to capture the exhaled anesthetic so that others in the room are not affected by escaping anesthesia.

Many children experience varying levels of fear and associated trauma by the use of forceful restraint on an operating room table by strange adults while a "stinky" mask is shoved onto their face. For many children, this produces a feeling of suffocation; even a child who has been cooperative up until that point may begin to fight and cry while their parent, who has accompanied them back to the operating room, looks on in horror. Such a combination of effects is not conducive to a pleasant induction experience for the child in the first event and increasingly so if the child should require a series of operations or treatments. One test documenting fear and anxiety is found in the article by Gomez et al., "Efficacy of Anesthetic Premedication in Pediatric Patients Using Oral Midazolam and Acetaminophen. Observational Study", *Rev. Colomb. Anesthesiol.*, vol. 41, No. 1, pp. 4-9 (2013). Postoperative behavioral changes related to stressful hospital experiences/induction of anesthesia include general anxiety, enuresis, night-time crying, and temper tantrums. These changes are usually transient but may persist for up to 1 yr. See Tan et al., Anaesthesia for the Uncooperative Child", *Continuing Education in Anaesthesia, Critical Care & Pain*, Vol. 10, No. 2, pp. 48-52 (2010).

A study reported by Kain et al. in "Distress During the Induction of Anesthesia and Postoperative Behavioral Outcomes", Anesthesia & Analgesia, vol. 88, issue 5, pp. 1042-1047 (1999) found a correlation between anxiety during induction of anesthesia and negative postoperative behavioral changes:

The frequency of negative postoperative behavioral changes decreased with time after surgery, and the frequency of negative postoperative behavioral changes increased when the child exhibited increased anxiety during the induction of anesthesia. Finally, we found a significant correlation (r) of 0.42 (P=0.004) between the anxiety of the child during induction and the excitement score on arrival to the postanesthesia care unit. We conclude that children who are anxious during the induction of anesthesia have an increased likelihood of developing postoperative negative behavioral changes. We recommend that anesthesiologists advise parents of children who are anxious during the induction of anesthesia of the increased likelihood that their children will develop postoperative negative behavioral changes such as nightmares, separation anxiety, and aggression toward authority.

The use of physical restraint of various degrees remains the recommended procedure for inducing anesthesia in the pediatric patient. See Tan et al., Anaesthesia for the Uncooperative Child", *Continuing Education in Anaesthesia, Critical Care & Pain*, Vol. 10, No. 2, pp. 48-52 (2010).

A number of potential solutions have been proposed to handle traumatic circumstances experienced by pediatric patients. For example, U.S. Pat. No. 4,896,666 teaches the use of a mask assembly for infants having a detachable pacifier. The pacifier is said to calm the infant without requiring an overly large mask. In one embodiment, the anesthetic gas is passed through an opening in the pacifier thereby reducing detection of the smells of the anesthetic gases. See also U.S. Pat. Nos. 6,776,157 and 8,671,934.

U.S. Pat. No. 5,697,363 teaches the use of a headpiece having headphone speakers and a chamber that can be positioned over the patient's nose for delivery of the anesthesia gas.

U.S. Pat. Nos. 5,865,172; 5,937,852 and 6,073,628 describe a masked induction system for pediatric patients with a rotatable impeller disposed in the attached tubing and connected to a "sensory patient stimulator" that interacts with inspiratory or expiratory flow of gas through the conduit. Also disclosed are embodiments that involve a thermal paint that changes the color of the stimulator and an inflatable stimulator.

U.S. Pat. No. 6,463,928 is also a mask-based system that is designed for use with pediatric patients. The induction tubing incorporates toy-like devices, such as whistles and balloons that are said to be activated by deep breathing while also capturing the exhaled anesthesia gases.

A history of attempts at various distraction techniques during pediatric induction of anesthesia can also be found in the article by Litman, "Allaying Anxiety in Children—When a Funny Thing Happens on the Way to the Operating Room", *Anesthesiology*, v. 115, no. 1, pp. 4-5 (2011).

The main problem with the prior art systems that rely on a mask is the mask itself. Placing the mask on the pediatric patient is an act that is confining, obstructs vision when the child most needs a wide field of view as adrenalin surges, feels confining and strange and suffocating, and introduces unpleasant smells. It is no wonder that the child reacts against such stimuli. One set of instructions to parents has this information for parents: "When going to sleep with a mask, children frequently try to take off the mask and/or become combative as they go to sleep. This is a normal reaction." and "Children often will cough, gag, cry, complain about the smell or say they cannot breathe. These reactions are common responses to placing a mask over a child's mouth and nose."

Parents, too, are affected by the reaction of their child to such mask-based pediatric induction techniques. See Zuwala et al., "Reducing Anxiety in Parents Before and During Pediatric Anesthesia Induction", *AANA Journal*, vol. 69, no. 1, pp. 21-25 (2001) and Kain et al., "Parental Presence during Induction of Anesthesia—Physiological Effects on Parents", Anesthesiology, vol. 98, no. 1, pp. 58-64 (2003). Traumatized parents may now feel inclined to voice their feelings about their induction experience in the post-procedure Hospital Consumer Assessment of Healthcare Providers and Systems (HCAHPS) survey.

The intent of the HCAHPS initiative is to provide a standardized survey instrument and data collection methodology for measuring patients' perspectives on hospital care. While many hospitals have collected information on patient satisfaction, prior to HCAHPS there was no national standard for collecting or publicly reporting patients' perspectives of care information that would enable valid comparisons to be made across all hospitals. In order to make "apples to apples" comparisons to support consumer choice, it was necessary to introduce a standard measurement approach. The result is the HCAHPS survey, which is also known as the CAHPS® Hospital Survey. (CAHPS is a federally registered trademark owned by the Agency for Healthcare Research and Quality in Rockville, Md.) HCAHPS is a core set of questions that can be combined with a broader, customized set of hospital-specific items. HCAHPS survey items complement the data hospitals currently collect to support improvements in internal customer services and quality related activities.

Three broad goals have shaped the HCAHPS survey. First, the survey is designed to produce comparable data on the patient's perspective on care that allows objective and meaningful comparisons between hospitals on domains that are important to consumers. Second, public reporting of the survey results is designed to create incentives for hospitals to improve their quality of care. Third, public reporting will serve to enhance public accountability in health care by increasing the transparency of the quality of hospital care provided in return for the public investment. With these goals in mind, the HCAHPS project has taken substantial steps to assure that the survey is credible, useful, and practical. This methodology and the information it generates are available to the public.

In May 2005, the National Quality Forum (NQF), an organization established to standardize health care quality measurement and reporting, formally endorsed the CAHPS® Hospital Survey. The NQF endorsement represents the consensus of many health care providers, consumer groups, professional associations, purchasers, federal agencies, and research and quality organizations. (Citation: http://goo.gl/mTs2g.)

With the development and acceptance of the HCAHPS survey, it will not be long before insurance companies start to use the HCAHPS scoring as a quality metrics tool for their reimbursement payments to hospitals. The federal department for Health and Human Services has already announced a pilot program to determine whether to include HCAHPS as part of its core set of quality measurements for children's health care. Parents who feel that their patient child has been traumatized or unnecessarily frightened by the techniques for pediatric induction of anesthesia may use their responses to the HCAHPS survey to voice their own trauma and distress to the detriment of the hospital.

It would be desirable to have a system and method for its use when inducing anesthesia in pediatric patients that would be free of the need to place a mask over the nose and mouth of pediatric patients and avoid the emotional reactions associated therewith by the patient as well as caregivers, parents and hospital staff.

It would also be desirable to have a system and method for its use that would provide distractions and/or fun activities for pediatric patients as anesthesia is induced.

SUMMARY OF THE INVENTION

It is an object of the invention to provide a mask-free system for pediatric induction of anesthesia and a method of operating the system to minimize trauma and anxiety by the patients and those who might themselves become anxious or affected by distress in the pediatric patient.

It is also an object of the invention to provide a mask-free induction system that uses a mouthpiece of a dimension calculated to hold open the patient's mouth sufficiently far enough that it encourages the child to take a deep breath through the mouth only and discourages breathing through the nose and, thereby, bypass the olfactory system (sense of smell) altogether.

In accordance with these and other objects of the invention that will become apparent from the description herein, a system according to the invention comprises: (a) an induction mouthpiece having an external shape and size sufficient to be disposed within the mouth of said patient; and (b) a first distraction device disposed within the gas flow path in an induction tube extending between the anesthesia source and the mouthpiece. The distraction device is positioned and connected to interact with gas flowing to and from the circuit tubing so that inhalation and/or exhalation through the circuit interacts with said distraction device and produces a perceivable effect that distracts the patient from the process of inducing anesthesia with a perceptible stimuli or game of challenge. Preferably, the system also incorporates a second distraction device into the mouthpiece that is of a type that is different than the first distraction device. A preferred second distraction device is a siren-type whistle that generates a sound having a pitch that is related to the speed of the gases passing through the mouthpiece.

A method of operating the present system so as to reduce patient anxiety in pediatric patients comprises the step of delivering one or more pharmaceutical gases in an amount calculated to induce anesthesia in said pediatric patient via an induction tube disposed within the mouth of said patient, said induction tube having an external shape and size sufficient to cause said patient to open his/her mouth sufficiently to encourage inhalation and exhalation through the patient's mouth in preference to his/her nose. An admixture of oxygen-nitrous oxide administered through the induction tube as a preliminary step to calm the child before switching to a more potent volatile anesthetic in order to induce general anesthesia.

The system of the present invention and its method of use help to avoid pediatric patient anxiety and trauma during the induction of anesthesia. The use of an oral tube for gas delivery eliminates the confining effects of a mask while also avoiding the unpleasant and unfamiliar odors of anesthesia gases. Pediatric patients who can respond to instructions reliably can be handed the induction tubing and mouthpiece and asked to position the mouthpiece thereby reducing anxiety by maintaining a sense of control having and eliminating the need for one of the hospital staff or the anesthesia care provider from positioning a mask on an anxious or frightened patient. The child may also be allowed to sit up which also decreases the sense of confinement and encourages a sense of active participation and cooperation. The result is a more peaceful induction procedure that reduces or eliminates the anxieties of the patient, parents, caregivers and hospital staff. Once the child is very sleepy or induced, he/she is gently laid in a supine position, the distraction device is easily removed, and subsequent induction procedures and intubation (placing of an endotracheal tube) can commence as per protocol. The use of a second distraction device that produces an audible sound also serves as a safety reminder that anesthesia gases are still flowing through the mouthpiece after induction.

DETAILED DESCRIPTION OF THE INVENTION

Figure 1:
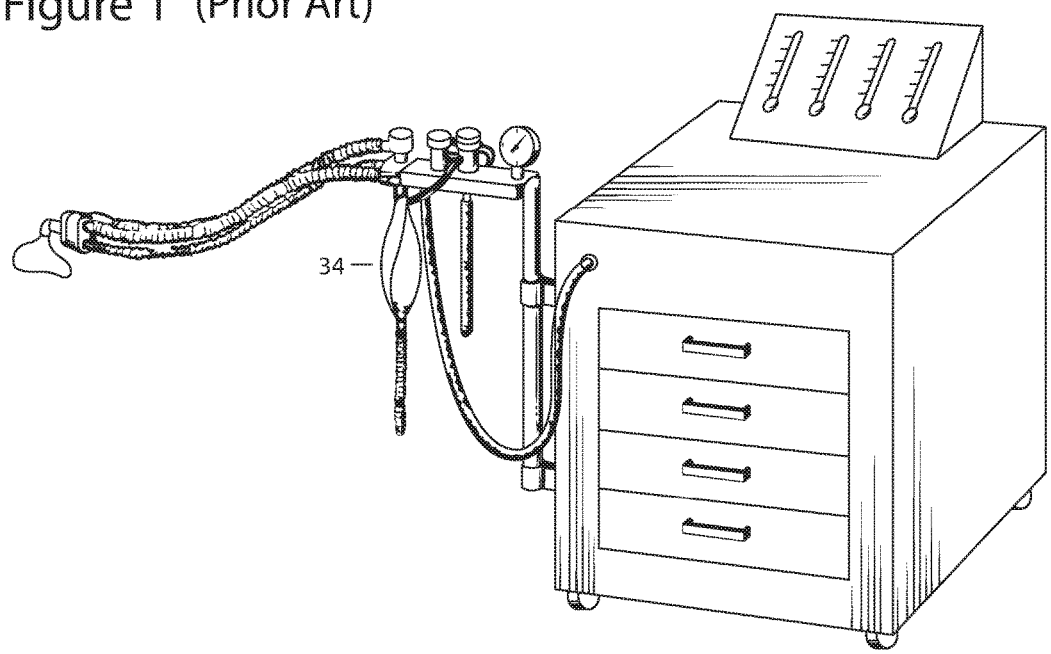
FIG. 1 shows a prior art anesthesia supply and reclamation system

The invention relates to a mask-free system for induction of anesthesia in a pediatric patient and for its method of use. An induction tube is positioned within the patient's mouth by the patient, if old enough, by the patient's parent or by a member of the hospital staff. This tube does not enclose the patient's nose or face and thereby eliminates the feeling of confinement and bypasses the olfactory senses.

Pediatric patients are generally 15 years of age or less. Such patients can be generally categorized further based on developmental age and their ability to respond to verbal instructions and different types of stimuli. For example, a 15 year old may be quite willing to follow verbal instructions in how to position the induction tube in their mouth and breathe only through their nose while the same might not be true for patients of two years or less. Spinning shapes may be quite sufficient for a toddler but more interaction or challenge would be required for a videogame-experienced 12 year old.

One article has noted that children older than five years usually have sufficient communication skills to allay fears through simple explanation or game play distraction while infants of less than one year do not appear to develop fears. The challenge of peaceful induction thus lies with children of 1-5 years who cannot understand explanations or games. See Trapp, "Techniques for induction of General Anesthesia in the Pediatric Dental Patient", *Anesth. Prog.*, vol. 39, pp. 138-141 (1992) at p. 139. Another separates pediatric patients into groups of less than one year, 1-3 years, 3-6 years, 7-12 years and 12+ years. See Tan et al., Anaesthesia for the Uncooperative Child", *Continuing Education in Anaesthesia, Critical Care & Pain*, Vol. 10, No. 2, pp. 48-52 (2010).

The system and method of the present invention is well suited for use with toddlers to teens or even adults who become anxious with mask-based anesthesia or intravenous administration. Inhalation of calming and/or volatile anesthetic gases through an oral tube addresses both fears while also avoiding the unfamiliar and often unpleasant odors associated with anesthetic gases, whether treating with scenting agents or not.

Risks of exhaled gases in a closed operating room are minimized by the use of an oral tube or tube mouthpiece that sufficiently open the jaws of the patient to 40-80% of maximum jaw displacement so that oral exhalation is more comfortable and natural than nasal exhalation. Also, said device would be introduced during the preoperative period so that the child may be instructed with the "toy" (device) and given the chance to practice "playing with it" in a proper fashion.

The system of the invention includes: (a) a conventional anesthesia gas delivery system; (b) a double corrugated circuit tubing from the anesthesia machine and circuit; (c) a connector, preferably with a gas sampling port to monitor exhaled carbon dioxide and gases, that connects the supply and return tubes to (d) a distraction device connected to (e) a mouthpiece used by the patient.

There are many varieties of anesthesia delivery systems that are suitable for the present invention. Some nonlimiting examples are described in detail in U.S. Pat. Nos. 3,814,091; 5,568,910; 5,743,257; 6,634,356; and 7,992,555. What each has in common is a subsystem for reclamation of anesthesia gases exhaled by the patient. Such systems typically include an inflatable bladder between the patient and the reclamation subsystem, e.g., reservoir breathing bag 34 in Prior Art FIG. 1 from FIG. 1 of U.S. Pat. No. 3,814,091. Bag 34 is intended to deflate as the patient inhales and inflate as the patient exhales. Bag 34 is the bag that anesthesiologists ask the patient to inflate during typical induction procedures thereby challenging the patient to exhale forcefully to effect a corresponding deep inhalation of anesthetic gases.

There are also many examples of connections for the supply (inspiration) and exhaust (expiration) lines that are suitable for use in anesthetic delivery systems. Some examples include conventional Y connectors, as in U.S. Pat. Nos. 3,814,091 and 5,546,930 as well as more elaborate designs such as those described in U.S. Pat. Nos. 3,933,171; 5,020,532; 5,743,257; 7,066,177; and 8,267,666. Useful connectors are intended to automatically provide low resistance flow streams from inspiratory to expiratory lines as the patient inhales and then exhales. A conventional Y connector is preferred for the present invention.

As noted above, the anesthesia delivery system of the present invention uses a mouthpiece, rather than a mask, and includes a distraction device inline with the induction tube or similarly associated with gas flow in the induction tube so that the distraction device interacts with the gas flow to or from the patient to generate a detectable effect.

A preferred distraction device is an inflatable breather bag (see, e.g., U.S. Pat. No. 3,859,997) that has been modified to accept a second connector at the opposite end of the bag. Suitable alternatives include easily inflated balloons and movable indicators as in the incentive spirometers of U.S. Pat. Nos. 4,391,283 and 6,238,353 as well as the computer-based game spirometer of US Patent Publication No. 2013/0303930.

Figure 2:
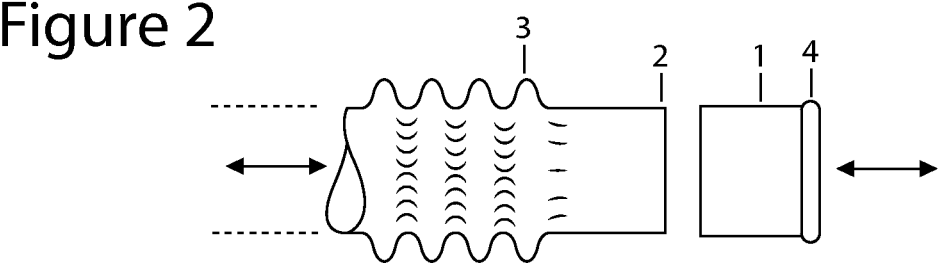
FIG. 2 illustrates a disposable mouthpiece affixed directly to the patient end of an anesthesia induction tube.
Figure 3:
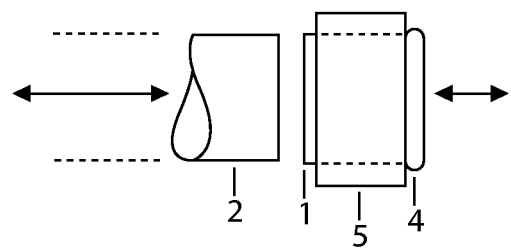
FIG. 3 shows a disposable mouthpiece covered by resilient padding for enhanced patient comfort in use.

One example of a suitable mouthpiece according to the invention is shown in FIG. 2 and includes a disposable mouthpiece 1 that fits over induction tube terminus end 2 of induction tube 3. Rounded end 4 softens end 4 when inserted into the pediatric patient's mouthy and avoids sharp edges from contact with the patient's tongue. A similar mouthpiece 1 is shown in FIG. 3 with a resilient covering 5 that cushions the patient's teeth and lips when mouthpiece 1 is inserted into the patient's mouth and held there during induction of anesthesia.

Figure 4:
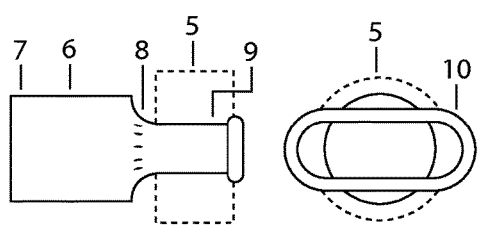
FIG. 4 depicts a disposable mouthpiece having an elongated oval shape that is optionally covered by resilient padding.

Mouthpiece 1 may exhibit almost any cross sectional shape or combination of shapes to provide both comfort and efficacy in use. The embodiments shown in FIGS. 2 and 3 exhibit a substantially circular cross sectional shape. Oval cross sectional shapes are also desirable. As shown in FIG. 4, combination mouthpiece 6 exhibits a connection end 7 exhibiting circular cross section and a diameter that fits over terminus end 2 of induction tube 3 and transitions in middle portion 8 to an insertion portion 9 exhibiting an extended oval shape in cross section and a rounded terminus end 10. An optional cushioning member 5 may be used to provide comfort to the patient as well as provide a mechanism by which the patient's jaws can be opened sufficiently to encourage exhalation by mouth rather than by nose.

Figure 5:
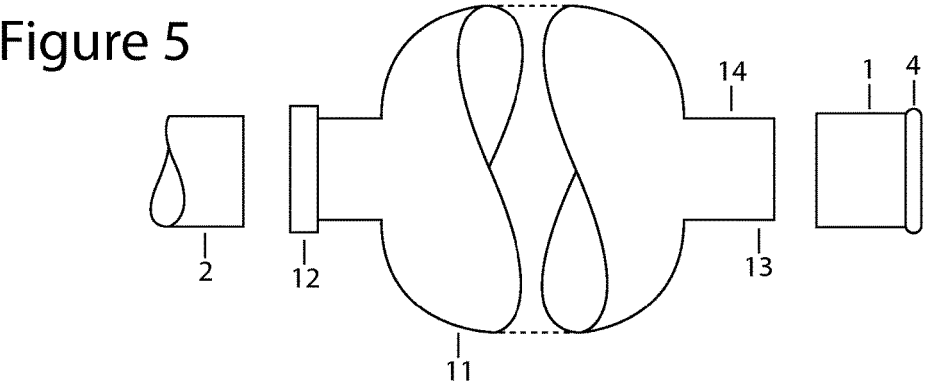
FIG. 5 is an exemplary distraction device made from a modified breathing bag having connections on both ends for inline connection between the mouthpiece and the terminus of the induction tube.

FIG. 5 illustrates a preferred distraction device based on an inflatable breather bag 11 that is connected at induction tube terminus end 2 and mouthpiece 1. Bag 11 may be a conventional reservoir breather bag used in conventional anesthesia systems having a circuit connection 12 but with a modification to include mouthpiece connection 13 or integrate mouthpiece 14 directly. Bag 11 may also be any type of balloon that, when at least partially pre-filled with anesthetic gases, is easily inflated by a pediatric patient or similar distraction device of one or more moving parts or electronic sensors that respond by moving a displayed character of an electronic display. Disposing this type of distraction device at the circuit end of the mouthpiece connection ensures that the pediatric patient can see the inflation and deflation effects of their efforts despite the location and layout of any treatment room.

Bag 11 can be made in 1, 1.5, or 2 liter size, in multiple colors or with pictures, giving the child the option of a choice and greater involvement in the induction process.

Figure 6:
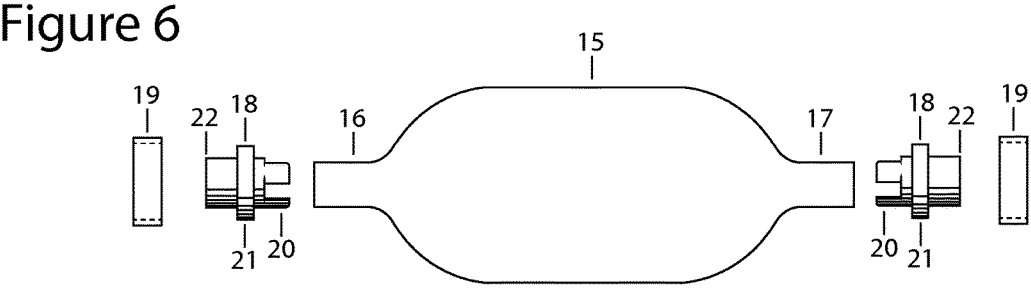
FIG. 6 illustrates the use of first and second connectors on opposite ends of an inflatable bag or balloon that can serve as a disposable distraction device.
Figure 7:
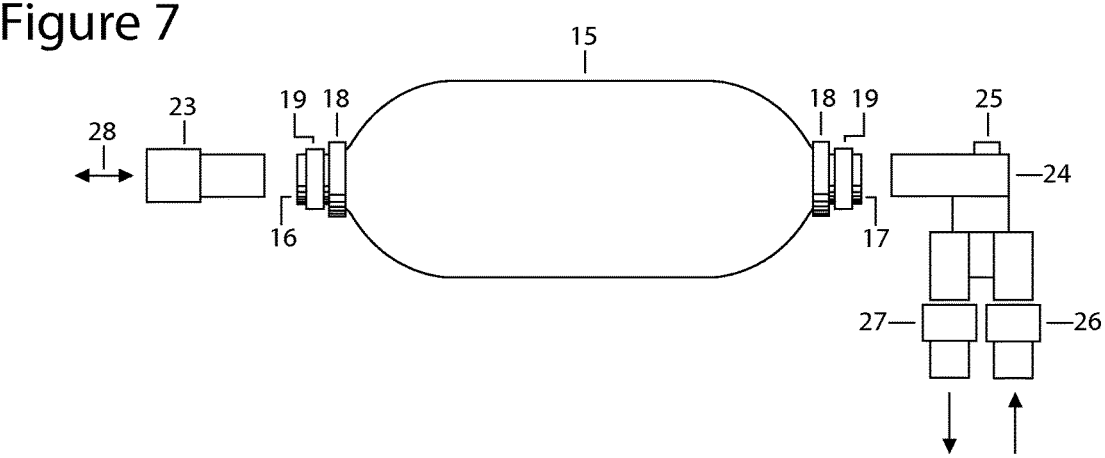
FIG. 7 shows a toy siren whistle inserted as an integral second, audible, distraction device/mouthpiece that then connects to the patient-side connector of an inflatable bag that serves as a first, visual, distraction device. The bag is connected at its opposite end to a conventional Y connector associated with a breathing circuit.

FIGS. 6 and 7 depict an inflatable balloon or adapted breather bag 15 having a first end 16 on the patient side of bag 15 and an opposing second end 17 on the circuit end of bag 15. The small ends 20 of rigid connectors 18 fit inside ends 16, 17 of bag 15 and over abutments 21 on connectors 18. Clip 19 then secured ends 16, 17 to the leading ends 22 of their respective connectors 18 to provide a structural connection. Clips 19 may be made of a rigid plastic or may be replaced by a length of adhesive or electrical tape having an adhesive strength adequate to secure ends 16, 17 around connectors 18.

As shown in FIG. 7, an optional, double-ended, substantially tubular, siren whistle 23 can also be used as a second distraction device and disposable mouthpiece for bag 15. Whistle 23 may be fitted snuggly into the connector 18 or integrally formed therewith to make a mouthpiece that also connects to the breather bag or balloon, e.g., siren 23 may be of a size sufficient to serve as both mouthpiece and second distraction device of an integral form and thereby secured to bag 15 directly with a suitable clip or tape.

On the circuit end 17 of bag 15, a Y connector 24 with sampling port 25 is fitted into connector 18. Inspiration fitting 26 and expiration fitting 27 are or have been connected to y connector 24 for delivery of gases 28 to and from the anesthesia circuit (not shown).

Available toy siren whistles come in plastic and metal versions and are well suited as second distraction devices of an audible type. A preferred whistle design is substantially tubular or stepped, tubular external design. Internally, a rotor with holes or slots having directional fins spins about an axis as gases pass through the rotor holes and produce an audible pitch that is proportional to the speed of the gas passing through the holes. An absence of lateral, external, vent holes in the outer casing (e.g., as in a railroad whistle) directs all anesthetic gases and exhaled contents to the patient or the rebreathing circuit. Preferred siren whistle designs are those shown in U.S. Pat. Nos. 1,955,815 and 2,092,942, the disclosures of which are specifically hereby incorporated by reference. As noted above, each has perforated ends and a movable, internal rotor with slanted vanes that catch the air passing through the device and cause the rotor to spin within the device and produce a sound as gas passes through the device upon inhalation as well as exhalation. The pitch of the sound correlates to the speed of the rotor and the strength of the inhalation or exhalation. The sound and its changes of pitch encourage deep inhalations of anesthetic gases by the patient.

The whistles may be provided in various colors or character images to enhance the fun and playful aspects of anesthesia induction. The whistle can also be used before the induction procedure to "practice" deep inhalations through the mouth and, later, sent home with the patient as a souvenir to remind them of their fun time in the operating room.

After induction, the whistle can also serve as a safety reminder for the anesthesia provider. The anesthesia provider will hear a whistling sound if gas flow continues to exit the device once the patient is asleep. This audible reminder, unlike the conventional mask, will prompt the anesthesia provider to turn the flows of the machine down or turn off the anesthetic agents, thereby decreasing the likelihood that anesthetic continues to be released into the room. The conventional mask has no reminder alarm system and is set aside in order to intubate (place the breathing tube into) the patient.

The process of using the system of the present invention allows the pediatric patient a measure of control over the induction process. Such control is most effective with pediatric patients of an age sufficient to follow verbal instructions and to grasp the induction device, e.g., patients of at least about three years of age. Juveniles and adults can also be treated by the present method if other induction methods—intravenous injection, oral medication or mask-based induction—are not tolerated or desired.

The process administers the anesthetic through a mouthpiece rather than a mask. This avoids the adverse reactions of many pediatric patients to the unpleasant odors that are typically associated with volatile anesthetics. The use of a mouthpiece also allows the pediatric patents to sit up, actively hold and position the mouthpiece in a more comfortable manner and without the use of external manipulations or forceful restraint by unknown hospital staff.

Preferably, a distraction device is connected to the mouthpiece or at a short distance therefrom so the patient can see and interact with the assembly during the induction process. With the device literally right in front of their eyes, the distraction device cannot be ignored and can be an effective device to divert the patient's attention to an activity that is fun and engaging even if only for the 20-30 seconds needed to induce anesthesia. After that, since the anesthesia circuit (i.e., corrugated tubing, elbow, Y-piece, sampling line) has not been tampered with, the device can be quickly disconnected and subsequent induction procedures and intubation can continue as per protocol.

The specific distraction device can be selected from a variety of devices. A simple and preferred device is an inflatable balloon that is connected between the anesthesia circuit and the mouthpiece, whether integrated with the balloon or separate, that is used by the patient. Children of three or more years know or can be shown how to blow up a balloon. Since the anesthesia circuit is always delivering a flow of oxygen and anesthetic gases, the balloon is always inflated, but the inhalation and exhalation still has a visible effect. Preferably, the balloon has a large enough volume that even children blowing through a relatively large diameter tube (e.g., within about 1-3 cm) can manifest a visible inflation effect. Such balloons are also light enough that they can be held and manipulated by pediatric patients without material assistance from others.

The induction process of the present invention also contemplates a stage 1 administration of a sub-anesthesia dose of a low potency anesthetic, such as nitrous oxide, followed by an anesthetic dose of a high potency anesthetic. The low potency anesthetic not only calms the pediatric patient but also enhances alveolar uptake of the high potency anesthetic. See Duarte et al., "Nitrous Oxide Use in Children", *Rev. Bras. Anestesiol.*, vol. 62, no. 3, pp. 451-467 (2012).

EXAMPLE

A pediatric patient was scheduled for anesthesia for an upcoming operation. The patient was only 5 years old and very scared, crying, almost traumatized from a history of mask-based anesthesia inductions and surgical procedures. The patient started to cry upon seeing the anesthesia provider, clinging to her mother and repeating over and over "No mask, no mask!" She knew from her history of procedures that anesthesia providers always used a mask with its associated odors and its encompassing feel to deliver the anesthesia. This patient fell into that category.

The terror in the patient's eyes was palpable. She clung to her mother so tightly that we couldn't get her on the table. Something had to be done.

The mother sat in a chair with the patient in her lap. An extra breathing bag of a one liter capacity with a smooth connector on the top was modified with a small hole at the bottom that was just large enough so the connector on the end of the corrugated induction tubing of the breathing circuit could fit snuggly into it and be secured with tape. The smooth connector was of a size that worked as an integrated mouthpiece for the patient.

A source of an oxygen/nitrous mixture was activated to fill this breathing bag through the connector at the bottom; a hand was placed at the oral mouthpiece to inflate like a balloon as well as prevent leakage of anesthetic into the room. The anesthetic-filled bag was then handed to the patient who was still screaming and yelling that she did not want a mask. The patient was then asked, "Do you want to blow up the balloon?"

The patient took the oxygen/nitrous oxide filled bag and instinctively placed her lips around the connector on the top, took a breath of the nitrous/oxygen admixture and blew. Her expired breath helped to inflate the bag and traveled back to the anesthesia machine to the scavenger as it would with mask induction. After the big exhalation to blow up the balloon, she naturally followed up with a deep inhalation of the oxygen/nitrous oxide. As the crying ceased, she took two more deep breaths of the nitrous as she watched her balloon "inflate" and then she started to giggle. The nitrous oxide was then turned off and replaced with a supply of an effective, volatile anesthetic (such as sevoflurane, desflurane, halothane and similar general anesthetics) to induce anesthesia.

The volatile anesthetics traditionally used to induce mask anesthesia (sevoflurane and halothane) are known to exhibit extremely unpleasant odors. Actually, they stink, even when poorly disguised with a variety of flavored scents and lip balms to hide the noxious anesthetic. Sometimes, pediatric patients who had been cooperative with mask-based induction up until that point will suddenly become combative once they smell the anesthetic. They start to fight and thrash about, trying to get away from it while the hospital staff members must physically restrain them, with their parents looking on and exhibiting obvious concern and anxiety. Traditionally, anesthesia providers have tried to comfort the parents by telling them "This is all quite normal." Nonetheless, more than one parent has left the operating room in tears out of concern for their child.

In the present example, however, the patient did not even smell the anesthetic gas because she wasn't breathing through a mask. With the mouthpiece, she quickly and easily fell asleep. Her mother did not exhibit the signs of trauma that frequently accompany pediatric inductions. In fact, she asked if we would do the same for her daughter on her next visit to the operating room. The staff were visibly relieved that the induction went so smoothly.

It will be understood by those in this art that the embodiments described herein in detail are preferred embodiments that are not to be construed as limitations on the scope of the appended claims.

All patents and publications that are identified herein are hereby incorporated by reference.

What is claimed is:

1. A mask-free method for induction of anesthesia in a pediatric patient, by a method that comprises the steps of:
    allowing said pediatric patent or the patient's parent to position within the patient's mouth a mouthpiece of a mask-free induction device, said induction device comprising:
    (a) a mouthpiece sufficiently large to cause said patient to open the patient's mouth and encourage inhalation and exhalation through the patient's mouth in preference to the patient's nose, wherein said mouthpiece is attached to
    (b) a first distraction device that is attached to said mouthpiece at a patient end of said first distraction device and, at an opposing circuit end, to an anesthesia circuit of an anesthesia machine, wherein said anesthesia circuit comprises
        (i) an inspiration line that supplies anesthesia gases to said mouthpiece and
        (ii) an expiration line that captures expired gases and returns the expired gases to said anesthesia machine, wherein said expiration line is connected to said inspiration line with a first connection fitting of a Y-connector, said expiration line is connected to a second connection fitting of said Y-connector, and a third connection fitting of said Y-connector that is attached to the circuit end of said first distraction device, wherein said first distraction device interacts with air flow through said mouthpiece to provide a distraction to said pediatric patient during inhalation and/or exhalation, and
    administering one or more pharmaceutical gases to said mouthpiece through said anesthesia circuit.

2. A method according to claim 1 wherein said mouthpiece is directly connected to said patient end of said first distraction device so that inhalation and/or exhalation through said mouthpiece interacts with said first distraction device and produces a perceivable effect that distracts said pediatric patient from the process of inducing anesthesia.

3. A method according to claim 2 wherein said first distraction device comprises an inflatable bag that inflates due to gas exhaled by said patient.

4. A method according to claim 3 wherein said mouthpiece incorporates a second distraction device within said mouthpiece, wherein said second distraction device is attached to a patient side end of said inflatable bag.

5. A method according to claim 4 wherein said second distraction device comprises a siren whistle.

6. A method according to claim 5 wherein said mouthpiece is integral in construction with said whistle.

7. A method according to claim 4 further comprising:
in advance of administering anesthesia, allowing said pediatric patient to play with said mouthpiece with said second distraction device before attachment to said inflatable bag.

8. A method according to claim 1 wherein the administering step comprises:
administering to said patient a sub-anesthesia amount of a low potency anesthetic through said mouthpiece in advance of administering a high potency anesthesia.

9. A mask-free system for induction of anesthesia in a pediatric patient, said system comprising:
a. an anesthesia circuit having a source providing one or more pharmaceutically acceptable anesthesia gases and a return for expired gases, said anesthesia circuit comprising: (a) an induction tube of an inspiration line that supplies anesthesia gases to a mouthpiece connected to a terminal end of said induction tube and without a mask, and (b) an expiration line that captures and returns expired gases to an anesthesia machine, wherein said expiration line is connected to said inspiration line with a Y connector;
b. said mouthpiece receiving anesthesia gases from said inspiration line and having an external shape and size sufficient to be disposed within the mouth of said pediatric patient and cause said patient to open said mouth sufficiently to encourage inhalation and exhalation through the patient's mouth in preference to the nose, said mouthpiece being free of association with a mask or covering of said patient's nose;
c. a first distraction device having a patient side end connected to said mouthpiece and an anesthesia side end connected to said Y-connector, said first distraction device being disposed within a gas flow path between the anesthesia source and the mouthpiece, said first distraction device located so as to interact with gas flowing out of said mouthpiece so that exhalation through said mouthpiece by said pediatric patient interacts with said distraction device and produces a perceivable effect that distracts said pediatric patient from the process of inducing anesthesia.

10. A system according to claim 9 wherein said Y connector is connected to an anesthetic circuit end of said distraction device, said Y connector having an input port for gases from said anesthesia source, an output port for return of exhaled gases from said patient to said anesthesia machine, and a sampling port.

11. A system according to claim 9 wherein said mouthpiece comprises a siren whistle as a second distraction device.

12. A system according to claim 9 wherein said first distraction device comprises an inflatable bag.

13. A system according to claim 9 wherein said first distraction device comprises an inflatable bag receiving said gases from said source, and
said system further comprises a second distraction device comprising a whistle that is connected to a patient side of said inflatable bag and which serves as said mouthpiece.

14. A mask-free induction device comprising:
(a) an inflatable bag having an anesthesia circuit connector at a circuit end of said bag and a mouthpiece connector at an opposite, patient-side end of said bag; and
(b) a mouthpiece comprising a whistle fitted to said mouthpiece connector, said mouthpiece having a circular or oval shape, said mouthpiece having a rounded terminal end to avoid sharp edges from contacting the patient's tongue when inserted into the patient's mouth.

15. A mask-free induction device according to claim 14 wherein said mouthpiece is integral with said whistle.

* * * * *